United States Patent
Verfaillie et al.

(10) Patent No.: US 9,388,388 B2
(45) Date of Patent: Jul. 12, 2016

(54) METHODS FOR MAKING CELLS WITH AN EXTRA-EMBRYONIC ENDODERMAL PRECURSOR PHENOTYPE

(75) Inventors: Catherine M. Verfaillie, Leuven (BE); Bert Binas, Gyeonggi-do (KR)

(73) Assignees: Katholieke Universiteit Leuven (BE); Hanyang University of Korea (KR)

( * ) Notice: Subject to any disclaimer, the term of this patent is extended or adjusted under 35 U.S.C. 154(b) by 321 days.

(21) Appl. No.: 13/996,248

(22) PCT Filed: Jan. 30, 2012

(86) PCT No.: PCT/IB2012/000413
§ 371 (c)(1),
(2), (4) Date: Nov. 15, 2013

(87) PCT Pub. No.: WO2012/104731
PCT Pub. Date: Aug. 9, 2012

(65) Prior Publication Data
US 2014/0057313 A1    Feb. 27, 2014

Related U.S. Application Data

(60) Provisional application No. 61/437,957, filed on Jan. 31, 2011.

(51) Int. Cl.
*C12N 5/00* (2006.01)
*C12N 5/074* (2010.01)
*C12N 5/073* (2010.01)
*G01N 33/50* (2006.01)

(52) U.S. Cl.
CPC ............ *C12N 5/0696* (2013.01); *C12N 5/0603* (2013.01); *C12N 5/0605* (2013.01); *C12N 5/0607* (2013.01); *C12N 2500/02* (2013.01); *C12N 2501/11* (2013.01); *C12N 2501/135* (2013.01); *C12N 2501/235* (2013.01); *G01N 33/5008* (2013.01)

(58) Field of Classification Search
CPC ............... C12N 5/0605; C12N 5/0603; C12N 2501/135
See application file for complete search history.

(56) References Cited

PUBLICATIONS

Debeb et al. PLOS One 4(9):1-13.*
Artus et al. Development and Stem Cells 137:3361-3372, Oct. 2010.*
Decision on Motions; Patent Interference No. 105.953 SGL, Tech Center 1600; filed Sep. 26, 2014.

* cited by examiner

*Primary Examiner* — Marcia S Noble
(74) *Attorney, Agent, or Firm* — Tarolli, Sundheim, Covell & Tummino LLP

(57) ABSTRACT

The invention is directed to methods for making cells in vitro that have an extra-embryonic endodermal precursor phenotype. The method involves culturing cells from blastocysts under specific defined conditions.

7 Claims, No Drawings

METHODS FOR MAKING CELLS WITH AN EXTRA-EMBRYONIC ENDODERMAL PRECURSOR PHENOTYPE

FIELD OF THE INVENTION

The invention is directed to methods for making cells in vitro that have an extra-embryonic endodermal precursor phenotype. The method involves culturing cells from blastocysts under culture conditions as described herein. A cellular feeder layer is not necessary under these conditions.

BACKGROUND OF THE INVENTION

Before implanting into the uterine wall, the mammalian conceptus specifies the cell types that are the founders of trophoblast, extra-embryonic endoderm, and fetus. The first morphologically distinct cell type of the trophoblast lineage is the trophectoderm, which becomes discernible at the morula stage and gives rise to the placental trophoblast. The first morphologically distinct cell type of the extra-embryonic endoderm is the primitive endoderm, which at the late blastocyst stage becomes visible as a cell layer on the mural surface of the Inner Cell Mass (ICM) and gives rise to the yolk sac endoderm with its visceral and parietal components. Finally, the first morphologically distinct cell type of the fetal lineage is the epiblast, which constitutes the remainder of the late ICM and gives rise to amnion, extra-embryonic mesoderm, and embryo proper (Nagy et al., *Manipulating the Mouse Embryo: A Laboratory Manual*, 3$^{rd}$ ed, Cold Spring, N.Y.: Cold Spring Harbor Laboratory Press p. 764 (2002)).

Cultured cell lines that maintain or acquire pre- or peri-implantation embryo cell type are the well-known mouse embryonic stem (ES) cells (Evans et al., *Nature* 292:154-156 (1981) and Martin G., *Proc Natl Acad Sci USA* 78:7634-7638 (1981)), which closely resemble the nascent epiblast (Nichols et al., *Development* [Epub ahead of print] Aug. 26 (2009)).

The situation has been less clear regarding cell lines representing extra-embryonic endoderm lineages. Cell lines with trophoblastic (and perhaps extra-embryonic-endodermal) differentiation potential (Buehr et al., *Biol Reprod* 68:222-229 (2003); Fandrich et al., *Nat Med* 8:171-178 (2002); and Epple-Farmer et al., *Cell Transplant April* 29.pii: CT-1966 [Epub ahead of print]) have been derived from rat blastocysts. Furthermore, extra-embryonic endoderm stem cell lines called "XEN cells" ("XEN" for extra-embryonic endoderm) have been isolated from mouse blastocysts (Kunath et al., *Development* 132:1649-1661 (2005)). These XEN cells can efficiently contribute to parietal endoderm in vivo, but they did not efficiently integrate into the visceral endoderm (i.e., the committed extra-embryonic endoderm precursor). XEN cells do not express the transcription factor Oct4 (Kunath et al. (2005)) that is found in all cells of the early ICM (Ovitt et al., *Mol Hum Reprod* 4:1021-1031 (1998)).

One analysis of mouse blastocysts has raised the possibility that the committed extra-embryonic endoderm precursor exists already in the early ICM (Chazaud et al., *Dev Cell* 10:615-624 (2006) and Kurimoto et al., *Nucleic Acids Res* 34:e42 (2006)).

Debeb et al., *PLoS One* 4: e7216 (2009) has shown that, from rat blastocysts, cell lines with extra-embryonic endoderm identity can be derived that are distinguished from XEN cells by a less mature marker spectrum (including Oct4) and a better ability to form visceral endoderm (in addition to parietal) in vitro and in vivo. These cells appear to represent the first committed step of the extra-embryonic endoderm lineage, and were, therefore, named XEN-F cells ("F" for precursor).

Debeb generated the rat cell lines that express extra-embryonic endodermal precursor markers by explanting the blastocysts onto mitotically-inactivated primary embryo fibroblasts (generally designated in the industry as a "feeder layer").

SUMMARY OF THE INVENTION

The inventors have discovered how to generate cell lines that express extra-embryonic endodermal precursor genes and which can be grown from blastocysts without the need for a cellular feeder layer.

The invention is directed to methods for making cells in vitro that have an extra-embryonic endodermal precursor phenotype. The method involves culturing cells from blastocysts under specific defined conditions. A cellular feeder layer is not necessary under these conditions.

These extra-embryonic endodermal precursor cells proliferate without obvious senescence and differentiate in vitro into cell types that include, but are not limited to, endothelial, smooth muscle, hepatocyte-like and neural progenitor cell-like cells. They express a number of pluripotency-related transcription factors that include, but are not limited to, one or more of oct4, rex-1, and ESC-associated genes, such as Ecats. They also express endodermal transcription factors that include, but are not limited to, one or more of Gata4, Gata6, Sox7, Sox17, Foxa2 and HNF1β, and HNF4α.

In an embodiment of the invention, blastocysts are cultured in a cell culture medium containing platelet-derived growth factor (PDGF) under conditions of reduced oxygen. In the case of rodent cells, the medium may contain leukemia inhibitory factor (LIF). Epidermal growth factor (EGF) may be added to the culture medium. Dexamethasone may be added to the culture medium.

Any basal medium can be used. In a specific exemplified embodiment, the basal medium is 60% DMEM (LG) and 40% MCDB-201.

Conditions for reduced oxygen include, but are not limited to, oxygen conditions lower than ambient oxygen, i.e., less than about 20%. In one embodiment, the oxygen concentration is about 10% or less. In a specific exemplified embodiment, the oxygen concentration is about 5%. However, lower oxygen can range from about 2% to about 19% with 1% increments in between, such as about 3%, 4%, 5%, 6%, 7%, 8%, 9%, etc.

Serum concentration (when serum is added) can range from about 1% to up to about 19%. In one embodiment, the serum concentration is about 2-5%. In a specific exemplified embodiment, the serum concentration is 2%. Medium may also be serum-free.

In a specific exemplified embodiment, PDGF-BB is added to the culture medium. Equivalents of this growth factor are also contemplated. Concentrations of PDGF may range from about 5-about 50 ng/ml. In a specific exemplified embodiment, the concentration of PDGF is 10 ng/ml.

When cells with the extra-embryonic endodermal precursor phenotype have grown out from the blastocyst and attached to a substrate, the cells can be maintained at lower densities. These include, but are not limited to, about 50 cells/cm$^2$-about 500 cells/cm$^2$. In a specific exemplified embodiment, the density is maintained by replating cells at a density of about 100-200 cells/cm$^2$ after, on average, about 4-6 population doublings.

In one embodiment, the substrate upon which the blastocysts are cultured and to which the cells with the extra-embryonic endodermal precursor phenotype attach is coated. Coatings include, but are not limited to, collagens and fibronectins. In a specific exemplified embodiment, the coating is fibronectin.

The cells can be used to produce differentiated progeny with an ectodermal, endodermal, or mesodermal phenotype. Thus, according to the invention, these cells can differentiate in vitro into cell types of one or more of the embryonic germ layers, such as two or even three.

Several extra-embryonic tissues can be made from extra-embryonic endodermal precursor cells, including parietal and visceral endoderm, as well as some cells of the trophoblast. These cells are important for embryo implantation and to form the yolk sac. Malfunction of these cells is also implicated in spontaneous abortion. Therefore, the extra-embryonic endodermal precursor cells, in particular human cells, are useful to study the mechanisms of implantation and defects that result in spontaneous abortion. This could be done by, for example, altering gene expression (by up- or down-regulating a desired gene) and assessing the effect.

Methods for isolating blastocysts are well known in the art. Blastocysts can be isolated from any mammalian species, including human. Blastocysts need not be isolated from an intact animal but can be made by in vitro methods involving in vitro fertilization.

DETAILED DESCRIPTION OF THE INVENTION

Definitions

As used herein, the terms below are defined by the following meanings.

"A" or "an" means herein one or more than one; at least one. Where the plural form is used herein, it generally includes the singular.

A "cell bank" is industry nomenclature for cells that have been grown and stored for future use. Cells may be stored in aliquots. They can be used directly out of storage or may be expanded after storage. This is a convenience so that there are "off the shelf" cells available for administration. The cells may be stored in a pharmaceutically-acceptable excipient or they may be mixed with an appropriate excipient when they are released from storage. Cells may be frozen or otherwise stored in a form to preserve viability. In one embodiment of the invention, cell banks are created in which the cells have been selected for achieving desired effects. Following release from storage, it may be preferable to again assay the cells for the effects. This can be done using any of the assays, direct or indirect, described in this application or otherwise known in the art. Then cells having the desired effects can then be used.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of and similar phrases using words of the root "comprise" are used herein as synonyms of "comprising" and have the same meaning.

"Comprised of" is a synonym of "comprising" (see above).

"Expansion" refers to the propagation of a cell without differentiation.

Use of the term "includes" is not intended to be limiting.

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only the extra-embryonic endodermal precursor cells. Rather, the term "isolated" indicates that the cells are not in their natural tissue environment and are present at a higher concentration as compared to the normal tissue environment. Accordingly, an "isolated" cell population may further include cell types in addition to the extra-embryonic endodermal precursor cells and may include additional tissue components. This also can be expressed in terms of cell doublings, for example. A cell may have undergone 10, 20, 30, 40 or more doublings in vitro or ex vivo so that it is enriched compared to its original numbers in vivo or in its original tissue environment.

According to the present methods, when the extra-embryonic endodermal precursor cells grow out from the blastocyst, they are highly enriched. They are substantially homogeneous at first passage. This means that they are greater than about 75% homogeneous, for example, about 80%, 90%, 95%, or even up to 100%.

"Self-renewal" refers to the ability to produce replicate daughter stem cells having differentiation potential that is identical to those from which they arose. A similar term used in this context is "proliferation."

Cell Culture

In one embodiment, present invention provides a culture method for isolating and expanding the cells, which can involve culturing the cells in serum-free or low-serum medium containing insulin, selenium, bovine serum albumin, linoleic acid, dexamethasone, and platelet-derived growth factor. The serum-free or low serum medium may be low-glucose DMEM in admixture with MCDB. The insulin may be present at a concentration of from about 10 to about 50 µg/ml. The serum-free or low-serum medium may contain an effective amount of transferrin at a concentration of greater than 0 but less than about 10 µg/ml, the selenium may be present at a concentration of about 0.1 to about 5 µg/ml, the bovine serum albumin may be present at a concentration of about 0.1 to about 5 µg/ml, the linoleic acid may be present at a concentration of about 2 to about 10 µg/ml and the dexamethasone may be present at a concentration of about 0.005 to 0.15 µM. The serum-free medium or low-serum medium may contain about 0.05-0.2 mM L-ascorbic acid. The serum-free medium or low-serum medium may contain about 5 to about 15 ng/ml platelet-derived growth factor, 5 to about 15 ng/ml epidermal growth factor, 5 to about 15 ng/ml insulin-like growth factor, 10-10,000 IU leukemia inhibitory factor. The present invention further provides a cultured clonal population of the cells cultured according to the above-described method.

In one embodiment, cells are plated onto culture dishes coated with 5-115 ng/ml (preferably about 7-10 ng/ml) serum fibronectin or other appropriate matrix coating. Cells are maintained in Dulbecco Minimal Essential Medium (DMEM) or other appropriate cell culture medium, supplemented with 1-50 ng/ml (preferably about 5-15 ng/ml) platelet-derived growth factor-BB (PDGF-BB), 1-50 ng/ml (preferably about 5-15 ng/ml) epidermal growth factor (EGF), 1-50 ng/ml (preferably about 5-15 ng/ml) insulin-like growth factor (IGF), or 100-10,000 IU (preferably about 1,000 IU) LIF, with $10^{-10}$ to $10^{-8}$ M dexamethasone or other appropriate steroid, 2-10 µg/ml linoleic acid, and 0.05-0.15 µM ascorbic acid. Other appropriate media include, for example, MCDB, MEM, IMDM, and RPMI. Cells can either be maintained without serum, in the presence of 1-2% fetal calf serum, or, for example, in 1-2% human AB serum or autologous serum.

Serum-free medium is also described in U.S. Pat. No. 7,015,037. Many cells have been grown in serum-free or low-serum medium. In this case, the medium is supplemented with one or more growth factors. Commonly used growth factors include, but are not limited to, bone morphogenic protein, basic fibroblast growth factor, platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference herein for teaching growing cells in serum-free medium.

A specific exemplified embodiment for culture medium components is shown in Subramanian et al. (*Methods Mol Biol* 363:55-78 (2010)) and Breyer et al., (*Exp. Hematol* 34: 1596-1601 (2006)), incorporated by reference, and in Examples 2 and 3.

Uses

In methods in which the cells are subjected to differentiation conditions to produce some of the differentiated cell types discussed in this application, many, if not most of those conditions are available to those of ordinary skill in the art. See for example, Mays et al. (*Expert Opinion Biol Ther* 2:173-184 (2007)) and links therein to differentiation protocols; hepatocytes (*J Clin Invest* 109:1291-302; hematopoietic (*J Exp Med* 204:129-39), smooth muscle (*J Clin Invest* 116: 3139-3149 (2006)). These differentiation conditions are incorporated herein by reference. Many differentiation conditions are in U.S. Pat. No. 7,015,037 and Mays et al. (above), incorporated by reference for these protocols.

Using appropriate growth factors, chemokines, and cytokines, cells can be induced to differentiate to form a number of lineages, including, for example, a variety of cells of mesodermal phenotype, cells of neuroectodermal phenotype (glial cells, oligodendrocytes, and neurons), and cells of endodeinial phenotype. These include osteoblasts, chondroblasts, adipocyte, cartilage and bone, skeletal muscle, smooth muscle, cardiac muscle, endothelial cells, hematopoietic cells, stromal cells, neuronal cells, and hepatocytes, beta cells, other endodermal epithelial cells.

The invention thus provides differentiated cells obtained from the cells described above, wherein the progeny may be a bone, cartilage, adipocyte, fibroblast, marrow stroma, skeletal muscle, smooth muscle, cardiac muscle, endothelial, epithelial, endocrine, exocrine, hematopoietic, glial, neuronal or oligodendrocyte cell. The differentiated progeny cell may be a skin epithelial cell, liver epithelial cell, pancreas epithelial cell, pancreas endocrine cell or islet cell, pancreas exocrine cell, gut epithelium cell, kidney epithelium cell, or an epidermal associated structure.

Methods of identifying and subsequently separating differentiated cells from their undifferentiated counterparts can be carried out by methods well known in the art. Cells that have been induced to differentiate using methods of the present invention can be identified by selectively culturing cells under conditions whereby differentiated cells outnumber undifferentiated cells. Similarly, differentiated cells can be identified by morphological changes and characteristics that are not present on their undifferentiated counterparts, such as cell size and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional upregulation of specific genes, differentiated cells often display levels of gene expression that are different from undifferentiated cells. Reverse-transcription polymerase chain reaction, or RT-PCR, also can be used to monitor changes in gene expression in response to differentiation. Whole genome analysis using microarray technology also can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads and combinations thereof. One embodiment of the present invention contemplates the use of FACS to identify and separate cells based on cell-surface antigen expression.

The differentiated progeny can be used to correct a genetic disease, degenerative disease, cardiovascular disease, metabolic storage disease, neural, or cancer disease process. They can be used to produce gingiva-like material for treatment of periodontal disease. They can be used to develop skin epithelial tissue derived from the cells that can be utilized for skin grafting and plastic surgery. They can be used to enhance muscle. They can be used to produce blood ex vivo for therapeutic use, or to produce human hematopoietic cells and/or blood in prenatal or post natal animals for human use. They can be used as a therapeutic to aid for example in the recovery of a patient from chemotherapy or radiation therapy in treatment of cancer, in the treatment of autoimmune disease, to induce tolerance in the recipient.

Neuroretinal progeny cells can be used to treat disease caused by among other things macular degeneration, diabetic retinopathy, glaucoma, retinitis pigmentosa.

Cardiomyocyte progeny can be used to treat cardiac diseases including, but not limited to, myocarditis, cardiomyopathy, heart failure, damage caused by heart attacks, hypertension, atherosclerosis, and heart valve dysfunction.

Neural progeny can be used to treat a disease involving CNS deficits or damage. Further the neuronally-differentiated progeny cell can be used to treat a disease involving neural deficits or degeneration including, but not limited to, stroke, Alzheimer's disease, Parkinson's disease, Huntington's disease, AIDS-associated dementia, spinal cord injury, and metabolic diseases affecting the brain or other nervous tissue.

Stromal cell progeny can be used to support the growth and differentiation of other cell types in vivo or in vitro, including, but not limited to, hematopoietic cells, pancreatic islet or beta cells, hepatocytes, and the like. Cartilage progeny can be used to treat a disease of the joints or cartilage, including, but not limited to, cartilage tears, cartilage thinning, and osteoarthritis. Osteoblast progeny can be used to ameliorate a process having deleterious effects on bone including, but not limited to, bone fractures, non-healing fractures, osteoarthritis, "holes" in bones cause by tumors spreading to bone such as prostate, breast, multiple myeloma, and the like.

Osteoblasts:

Cells that have been induced to differentiate to form bone cells can be used as cell therapy or for tissue regeneration in osteoporosis, Paget's disease, bone fracture, osteomyelitis, osteonecrosis, achondroplasia, osteogenesis imperfecta, hereditary multiple exostosis, multiple epiphyseal dysplasia, Marfan's syndrome, mucopolysaccharidosis, neurofibromatosis or scoliosis, reconstructive surgery for localized malformations, spina bifida, hemivertebrae or fused vertebrae, limb anomalies, reconstruction of tumor-damaged tissue, and reconstruction after infection, such as middle ear infection.

Chondrocytes:

Cells that have been induced to differentiate to form cartilage cells can be used for cell therapy or tissue regeneration in age-related diseases or injuries, in sports-related injuries, or in specific diseases, such as rheumatoid arthritis, psoriasis arthritis, Reiter's arthritis, ulcerative colitis, Crohn's disease, ankylosing spondylitis, osteoarthritis, reconstructive surgery of the outer ear, reconstructive surgery of the nose, and reconstructive surgery of the cricoid cartilage.

Adipocytes:

Cells that have been induced to differentiate to form adipocytes can be used in resculpting for reconstructive or cosmetic surgery, including but not limited to, breast reconstruction after mastectomy, reshaping tissue lost as a result of other surgery, such as tumor removal from the face or hand, breast augmentation, and reduction of wrinkles. Treatment of Type II diabetes is also applicable. Adipocytes thus derived can also provide an effective in vitro model system for the study of fat regulation.

Fibroblasts:

Fibroblast progeny can be used for cell therapy or tissue repair to promote wound healing or to provide connective tissue support, such as scaffolding for cosmetic surgery.

Skeletal Muscle:

Cells that have been be induced to differentiate to form skeletal muscle cells can be used for cell therapy or tissue repair in the treatment of Duchenne muscular dystrophy, Becker muscular dystrophy, myotonic dystrophy, skeletal myopathy, and reconstructive surgery to repair skeletal muscle damage.

Smooth Muscle:

Cells that have been induced to differentiate to form smooth muscle cells can be used for cell therapy or tissue repair in the treatment of developmental abnormalities of the gastrointestinal system, such as oesophageal atresia, intestinal atresia, and intussusception, and replacement of tissues after surgery for bowel infarction or colostomy. Smooth muscle cells can also be used for bladder or uterine reconstruction, neovascularization, repair of vessels damaged by, for example, atherosclerosis or aneurysm. Smooth muscle precursor cells (mesangial cells) can be used as an in vitro model for glomerular diseases or for cell therapy or tissue regeneration in diabetic neuropathy. Smooth muscle precursors can also be used to repair macula densa of the distal convoluted tubule or juxtaglomerular tissues.

Cardiomyocytes:

Cardiomyocytes can be used for cell therapy or tissue repair for treating heart tissue damaged following myocardial infarction, in conjunction with congestive heart failure, during valve replacement, by congenital heart anomalies, or resulting from cardiomyopathies or endocarditis.

Microglial Cells:

Microglial cells can be used to treat spinal cord injuries and neurodegenerative disorders, such as Huntington's disease, Parkinson's disease, multiple sclerosis, and Alzheimer's disease, as well as repair of tissues damaged during infectious disease affecting the central nervous system. Microglial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, and for regeneration after spinal cord injury.

Stromal Cells:

Stromal cells can be used as transplant cells for post-chemotherapy bone marrow replacement and bone marrow transplantation.

Endothelial Cells:

Endothelial cells can be used in the treatment of Factor VIII deficiency and to produce angiogenesis for neovascularization. Endothelial cells can also provide an in vitro model for tumor suppression using angiogenic inhibitors, as well as an in vitro model for vasculitis, hypersensitivity and coagulation disorders.

Hematopoietic Cells:

Hematopoietic cells can be used to repopulate the bone marrow after high-dose chemotherapy. Hematopoietic cells derived from the cells of the aggregate can be further differentiated to form blood cells to be stored in blood banks, alleviating the problem of a limited supply of blood for transfusions.

Neuroectodermal Cells:

Glial cells can be used to treat spinal cord injuries and neurodegenerative disorders, such as Huntington's disease, Parkinson's disease, multiple sclerosis, and Alzheimer's disease, as well as repair of tissues damaged during infectious disease affecting the central nervous system. Glial cells that have been genetically altered to produce cytokines can also be used for transplantation for the treatment of infectious disease in the central nervous system where access is limited due to the blood-brain barrier. Glial cells can also be used to produce growth factors or growth factor inhibitors for regeneration of nerve tissue after stroke, as a consequence of multiple sclerosis, amylotropic lateral sclerosis, and brain cancer, as well as for regeneration after spinal cord injury. Cells induced to form oligodendrocytes and astrocytes, for example, can be used for transplant into demyelinated tissues, especially spinal cord, where they function to myelinate the surrounding nervous tissues. The cells also can be used in cell replacement therapy and/or gene therapy to treat congenital neurodegenerative disorders or storage disorders such as, for instance, mucopolysaccharidosis, leukodystrophies (globoid-cell leukodystrophy, Canavan's disease), fucosidosis, GM2 gangliosidosis, Niemann-Pick, Sanfilippo syndrome, Wolman's disease, and Tay Sachs. They can also be used for traumatic disorders such as stroke, CNS bleeding, and CNS trauma; for peripheral nervous system disorders such as spinal cord injury or syringomyelia; for retinal disorders such as retinal detachment, macular degeneration and other degenerative retinal disorders, and diabetic retinopathy.

Ectodermal Epithelial Cells:

These cells can be used in cell replacement therapy and/or gene therapy to treat or alleviate symptoms of skin disorders such as alopecia, skin defects such as burn wounds, and albinism.

Endodermal Epithelial Cells:

Epithelial cells can be used in cell replacement therapy and/or gene therapy to treat or alleviate symptoms of several organ diseases. The cells could be used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders, such as inborn errors of the urea-cycle, for instance ornithine decarboxylase deficiency, citrullinemia, and arginosuccinic aciduria; inborn errors of amino acids and organic acids, such as phenylketonuria, hereditary tyrosinemia, and alphal-antitrypsin deficiency; and coagulation disorders such as factor VIII and IX deficiency. The cells can also be used to treat acquired liver disorders that result from viral infections. The cells can also be used in ex vivo applications, such as to generate an artificial liver, to produce coagulation factors and to produce proteins or enzymes generated by liver epithelium. The epithelial cells can also be used in cell replacement therapy and/or gene therapy to treat or alleviate symptoms of biliary disorders, such as biliary cirrhosis and biliary atresia. The epithelial cells can also be used in cell replacement therapy and/or gene therapy to treat or alleviate symptoms of pancreatic disorders, such as pancreatic atresia, pancreas inflammation, and alphal-antitrypsin deficiency. Further, as pancreatic epithelium, and as neural cells can be made, beta-cells can be generated. These cells can be used for the therapy of diabetes (subcutaneous implantation or intra-pancreas or intra-liver implantation. Further, the epithelial cells can also be used in cell replacement therapy and/or gene therapy to treat or alleviate symptoms of gut epithelium disorders such as gut atresia, inflammatory bowel disorders, bowel infarcts, and bowel resection.

Model System for Studying Pathways

The invention provides a method of using the extra-embryonic endodermal precursor cells to characterize cellular responses to biologic or pharmacologic agents involving contacting the cells with one or more biologic or pharmacologic agents and identifying one or more cellular responses to the one or more biologic or pharmacologic agents. Such agents may have various activities. They could affect differentiation, metabolism, gene expression, viability, and the like. The cells are useful, therefore, for e.g., toxicity testing and identifying differentiation factors.

Cells of the present invention are useful for further research into developmental processes, as well. WO 98/40468, for example, describes vectors and methods for inhibiting expression of specific genes, as well as obtaining the DNA sequences of those inhibited genes. Cells of the present invention can be treated with the vectors, such as those described, which inhibit the expression of genes that can be identified by DNA sequence analysis. The cells can then be induced to differentiate and the effects of the altered genotype/phenotype can be characterized.

Hahn et al. (*Nature* 400: 464-468 (1999)) demonstrated, for example, that normal human epithelial fibroblast cells can be induced to undergo tumorigenic conversion when a combination of genes, previously correlated with cancer, were introduced into the cells.

Control of gene expression using vectors containing inducible expression elements provides a method for studying the effects of certain gene products upon cell differentiation. Inducible expression systems are known to those of skill in the art. One such system is the ecdysone-inducible system described by No et al. (*Proc. Natl. Acad. Sci. USA* 93:3346-3351 (1996)).

Cells can be used to study the effects of specific genetic alterations, toxic substances, chemotherapeutic agents, or other agents on the developmental pathways. Tissue culture techniques known to those of skill in the art allow mass culture of hundreds of thousands of cell samples from different individuals, providing an opportunity to perform rapid screening of compounds suspected to be, for example, teratogenic or mutagenic.

For studying developmental pathways, cells can be treated with specific growth factors, cytokines, or other agents, including suspected teratogenic chemicals. Cells can also be genetically modified using methods and vectors known in the art. Furthermore, cells can be altered using antisense technology or treatment with proteins introduced into the cell to alter expression of native gene sequences. Signal peptide sequences, for example, can be used to introduce desired peptides or polypeptides into the cells. A particularly effective technique for introducing polypeptides and proteins into the cell has been described by Rojas, et al. (*Nature Biotechnology* 16: 370-375 (1998)). This method produces a polypeptide or protein product that can be introduced into the culture media and translocated across the cell membrane to the interior of the cell. Any number of proteins can be used in this manner to determine the effect of the target protein upon the differentiation of the cell. Alternately, the technique described by Phelan et al. (*Nature Biotech,* 16: 440-443 (1998)) can be used to link the herpes virus protein VP22 to a functional protein for import into the cell.

Cells can also be genetically engineered, by the introduction of foreign DNA or by silencing or excising genomic DNA, to produce differentiated cells with a defective phenotype in order to test the effectiveness of potential chemotherapeutic agents or gene therapy vectors.

Several extra-embryonic tissues can be made from extra-embryonic endodermal precursor cells, including parietal and visceral endoderm, as well as some cells of the trophoblast. These cells are important for embryo implantation and to form the yolk sac. Malfunction of these cells is also implicated in spontaneous abortion. Therefore, the extra-embryonic endodermal precursor cells, in particular human cells, are useful to study the mechanisms of implantation and defects that result in spontaneous abortion. This could be done by, for example, altering gene expression (by up- or down-regulating a desired gene) and assessing the effect. Thus, any compound could be tested for its effect (with the modified (i.e., up-regulated or down-regulated) or unmodified cell) on normal or abnormal implantation or embryonic development.

Kits

Cells can be provided in kits, with appropriate packaging material. For example, cells can be provided as frozen stocks, accompanied by separately packaged appropriate factors and media, as previously described herein, for culture in normal monolayer and/or as aggregates in the undifferentiated state. Additionally, separately packaged factors for induction of differentiation can also be provided.

The invention will be further described by reference to the following detailed example.

EXAMPLES

Example 1

These studies demonstrate that cells with an extra-embryonic endodermal precursor phenotype can be directly isolated from blastocysts. Culture conditions are from Breyer et al. and Subramanian et al. The cells can form yolk-sac like tumors when injected under the skin of immunodeficient mice. They can contribute to extra-embryonic (yolk-sac) tissues during morula aggregation (parietal endoderm, visceral endoderm, and trophoblast).

Cells with an Extra-Embryonic Endodermal Precursor Phenotype can be Isolated Directly from the Blastocyst Cells with an extra-embryonic endodermal precursor phenotype were isolated directly from blastocysts. Culture conditions were based on those in Breyer et al. and Subramanian et al. Blastocysts from Fisher and Wistar Kyoto rats were plated individually onto fibronectin-coated wells in the culture medium specified in Breyer et al and Subramanian et al. containing LIF, EGF and PDGF-BB, in reduced oxygen. One to ten days later, small, retractile cells emerged from the blastocysts. Typically, the attached blastocysts rapidly formed a "fried egg" structure consisting of giant trophoblast cells (the "egg white") and the ICM (the "yolk"). When the ICM was located at the fringe of that zone, the refractile cells emerged 1-2 days after blastocyst attachment and in the vicinity of the ICM; when the ICM was located in the center, migration of refractile cells out of attached blastocyst took up to 7 days or was not seen. In those rare cases when the refractile cells were already observed 1 or 2 days after plating, the blastocyst was still discernible. 5-7 days after the emergence of refractile cells, their number had increased to a few hundred. Then the trophoblast cells and other unidentified cell clumps were removed and the attached refractile cells were expanded into cell lines (5-10 million cells in two weeks) using the culture conditions described in Breyer et al. and Subramanian et al. All attempts were successful. Four cell lines of Wistar Kyoto background (lines named MAX5-MAX8) and four lines of Fischer background (lines named MAX1-MAX4) were derived. Immunostaining of the initial cell outgrowth demonstrated that most cells stained for Oct4 and Gata4, but were negative for Nanog. Upon passaging, cells retained the same phenotype and established cell lines stained positive for Oct4, Gata4, Gata6, Sox7 and Sox17 by IH, and 50-64% of cells were CD31/SSEA1-double positive by FACS. Furthermore, RT-qPCR analysis of cells isolated from the blastocyst (after 4-5 passages), demonstrated that all the MAX lines expressed Oct4, Gata4, Gata6, Sox7, Sox17, Hnf1β, but low levels of HNF4α, and undetectable levels of Nanog, Sox2 and Cdx2. The cell doubling time was 12-15 h. G-banding was done to assess cytogenetic abnormalities.

The inventors also performed colony formation assays in which LIF, PDGF, or EGF were individually omitted. Omission of LIF prevented colony formation completely, which is expected for rodent cells. Omission of PDGF resulted in a dramatic reduction. Omission of EGF or dexamethasone did not have visible effects. In line with the plating assays, removal of LIF from established cell lines resulted in growth arrest after 2 passages. This was associated with a significant decrease in Oct4 and Tbx3 mRNA expression and a significant induction of the visceral/parietal endoderm transcripts Hnf4α and Afp and the visceral endoderm transcript Tmprss2, suggesting default differentiation to a Xen-like phenotype or visceral endoderm (Chazaud et al., *Dev Cell* 10: 615-624 (2006)).

Three MAX lines tested from the eight isolated lines (MAX1 and MAX2 from Fisher rats and MAX8 from Wistar Kyoto rats) differentiated to smooth muscle-like, hepatocyte-like and neuroprogenitor-like cells.

Yolk Sac Tumor Formation and Contribution to Yolk Sac

MAX1 cells were transplanted under the skin of immunodeficient mice and formed yolk-sac like tumors, staining positive for laminin and pan-CK.

The developmental potential of GFP-labeled MAX cells in vivo was also tested by generating chimeras. Generation of rat MAX$^{GFP}$: mouse interspecies chimeras by morulae aggregation could be produced (16 chimeras/109 embryos). Xenogenic chimeras showed consistently that MAX descendants primarily contributed to the parietal yolk sac and not to the embryo proper or yolk sac mesoderm. GFP-positive cells were retrieved as dispersed parietal endoderm cells lining the inner side of the parietal yolk sac. Contribution to the trophoblast lineage was observed occasionally in chimeras that were kept within their deciduum. GFP-positive trophoblast cells were always in close contact with the Reichert's membrane lining the outer side of the parietal yolk sac. These GFP-positive trophoblast cells were not yet transformed into giant cells. Contribution to the visceral endoderm was more sporadic, and was observed in the distal-most visceral endoderm.

Discussion

The fact that MAX lines repopulate the visceral endoderm suggests that they represent the extra-embryonic precursor rather than primitive endoderm. Even though primitive endoderm gives rise to both visceral and parietal endoderm in vivo, cultured primitive endoderm cells lose this ability very rapidly (Gardner, *Philos Trans R Soc Land B Biol Sci* 312: 163-178 (1985)). The data indicate that the extra-embryonic precursor lineage identity can be continually maintained during the derivation process. Moreover, the experiments demonstrated that proliferation in vitro of the MAX cells depends on PDGF, consistent with the notion that within the ICM, cells expressing the PDGFRa receptor represent the extra-embryonic endodermal precursor population (Plusa et al. *Development* 135: 3081-3091 (2008)).

The microinjection experiments showed that MAX lines do not contribute to the fetus, i.e. they are committed to the extra-embryonic endoderm lineage, in accordance with their gene expression profile. On the other hand, the experiments demonstrated that MAX lines can convert robustly into mesodermal and hepatocyte-like cells in vitro.

The ability to isolate homogenous cell lines of MAX cells from rat blastocysts with high efficiency, that contribute to the parietal endoderm and visceral endoderm and the trophoblast layers, may allow further characterization of these different extra-embryonic cell compartments.

Materials and Methods

Derivation of MAX Cell Lines:

Nulliparous females of the inbred rat strains Fisher rats and Wistar Kyoto rats were mated with males of the same strain, and blastocysts were flushed out of uteri with PBS/20% FBS 4.5 days post coitum (vaginal plug detection time=0.5 days post coitum). The blastocysts (mostly still within the Zona pellucida) were plated into flat-bottom Nunc 4-well plates (1 blastocyst/well, 0.5 ml medium/well) under the culture conditions described in Subramanian et al. That is, the culture vessels were pre-coated with fibronectin, and the medium contained EGF, PDGF, LIF, and 2% pre-screened FBS, under reduced oxygen conditions. The vast majority of the blastocysts attached to the bottom of the culture vessel (1-7 days after plating), which in >50% of the cases was followed by rapid out-migration and proliferation of cells. Within 1 week after blastocyst attachment, what had become of the embryo (i.e., the trophoblasts and clumps with ES-like or unclear morphology), plus an abutting "safety zone", was carefully removed by suction using a glass capillary, leaving behind an essentially pure population of a few hundred cells. These latter cells were given a few hours to recover, and then the wells were gently washed with PBS, and the cells were trypsinized (0.05% trypsin/EDTA) and transferred into 6-well plates (1 well per original embryo) that were designated Passage no. 1. For the next passage, they were transferred into fibronectin-coated 100-mm dishes, and within 1-2 weeks after the initial trypsinization, the cells had grown to 6-8 100-mm dishes (Passages 3 or 4) and were frozen in liquid nitrogen or used to isolate RNA or DNA. During expansion and maintenance, care was taken to keep the cells in the exponential growth stage and avoid densities >$10^6$ cells/100-mm dish.

Colony Formation Assays:

The cells were trypsinized and centrifuged as for the regular passages, but washed an additional time in PBS by centrifugation in order to remove residual growth factors. The cells were plated into 6- or 12-well plates at the indicated densities and stained with Crystal Violet after 6 days.

LIF Withdrawal Studies:

Established MAX1 cells were cultured for 2 passages (4 day) with or without LIF, but with EGF and PDGF. Cells were enumerated on day 2 and 4, and RNA isolated on day 4 for determination of expression levels of Oct4, Tbx3, Afp, Hnf4α and Tmprrs2.

Flow Cytometry:

FACS staining protocols for cell surface marker expression were as described (Subramanian et al.). FACS analysis was done on a BD FACS Canto flow cytometer (BD Biosciences, Erembodegem, Belgium).

RT-qPCR:

For RNA isolation, the RNeasy Mini-kit/Micro-kit (Qiagen 74104 and 74004) was used. DNAse treatment was performed using Turbo DNAse kit (Ambion 1907). cDNA synthesis was performed from 1 µg of RNA with Superscript III First-Strand synthesis system (Invitrogen 18080-051). Real time PCR was performed with SYBR Green Platinum SYBR green qPCR Supermix-UDG (Invitrogen 11733-046) in an Eppendorf realplex/ABI 7000 (Eppendorf) equipment. Relative gene expression was calculated by the $2^{(-\Delta\Delta Ct)}$ method compared to undifferentiated cells (day 0), using GAPDH/Gadph as housekeeping gene.

Immunohistology of Cultured Cells:

Immunohistology was done as previously described (Roelandt et al. *PLoS One* 5: e12101 (2010)).

Immunostaining Cellular Material

MAX cells were cultured on fibronectin-coated well plates, washed with PBS and fixed for 10 minutes with a 4% formaldehyde solution. The samples were permeabilised in 0.2% Triton-X-100 in PBS, incubated with a blocking solution (5% serum in PBS) and stained overnight at 4° C. with primary antibodies diluted in DAKO antibody diluent. Then the samples were incubated for 30 minutes at room temperature with the secondary antibodies, dilution 1:500 in DAKO antibody diluent together with Hoechst 33258, diluted 1:2000, for nuclear staining.

In between the incubation steps the cells were washed with PBS containing 0.2% Triton-X-100. The immunostained cells were examined with a Nikon Eclipse Ti microscope using the 10×, 20× and 40× objectives, and using the Image pro plus software.

Morula Aggregation:

MAX1 and MAX2 cells were labeled with enhanced green fluorescent protein (EGFP) by lentiviral transduction. MAX single cell suspensions were prepared by trypsinization. Between 10-30 MAX1 and MAX2 cells were aggregated to Swiss morulae freed from the zona pellucida by acid Tyrode solution, and cultured in KSOM medium (Specialty Media) under pre-equilibrated mineral oil 37° C. in 5% CO2. The next day, embryos were transferred to the uterus of pseudopregnant Swiss females. Dissection of embryos at E7.5 and E8.5 was performed with special care to keep the parietal yolk sac intact. To detect chimerism in the trophectoderm lineage at E8.5, embryos where kept within the deciduum. Chimerism was detected by anti-GFP staining of paraffin sections.

Yolk Sac Tumor Formation:

1-2 million MAX1 and MAX2 cells were transplanted subcutaneously in Rag2(−/−)gamma(c)(−/−) mice with or without matrigel. Six to eight weeks after transplantation, the tumor became visible, animals were euthanized and the tumor harvested for further analysis.

In Vitro Differentiation Protocols:

Smooth Muscle Cell Differentiation

Differentiations were done in 12 well plates pre-coated with 100 ng/ml fibronectin. Differentiation was induced in serum-free medium described in Subramanian et al. supplemented with 2.5 ng/ml TGF-β1 and 5 ng/ml PDGF-BB. The starting cell density was 1500 cells/cm². On day 0, 2, 4, and 6, cells were harvested for RT-qPCR analysis of gene expression and immunofluorscence staining for smooth muscle-specific genes (Ross et al., *J Clin Invest* 116: 3139-3149 (2006)).

Hepatocyte-Like Cell Differentiation

Differentiations were done in 12 well plates pre-coated with 2% Matrigel diluted in PBS for 1-2 h at 37° C., in a 21% $O_2$—5.8% $CO_2$ incubator. The starting cell density of MAX cells was 50,000 cells/cm'. The cells were differentiated in basal differentiation medium, supplemented with the sequential cytokine (Aranguren et al., *J Clin Invest* 118: 505-514 (2008)); Roelandt et al., (2010); Ross et al., (2006); and Serafini et al., *J Exp Med* 204: 129-139 (2007)). Cells were harvested on day 0, 6, 14, and 20 for RT-qPCR analysis of primitive streak, immature and mature hepatocyte gene expression, and on day 20 for immunoflueoscence staining for hepatocyte specific proteins.

Neuroprogenitor-Like Cell Differentiation

Differentiations were done in 6-well plates coated with 0.1% gelatine solution for 30 min. Cells were plated at 1500 cells/cm² in N2B27 medium for 2 days, after which the medium was switched to NSE medium, all in a in a 5% $O_2$—5.8% $CO_2$ incubator. RNA was collected on days 0, 7 and 14 for gene expression analysis (Subramanian et al).

Cytogenetics

G-banding was performed (Subramanian et al).

Example 2

This disclosure is from Breyer et al.

Multipotent adult progenitor cells (MAPCs) have previously described as bone marrow-derived cells capable of differentiating into mesenchymal, neuroectodermal, and endodermal cells (Aranguren, et al., *J. Clin. Invest.* 118: 505-514 (2008); Breyer, et al., *Exp. Hematol.* 34: 1596-1601 (2006)). This Example, derived from Breyer et al. gives a protocol for their isolation and maintenance that has been successfully applied to producing the endodermal precursors.

Isolation and Maintenance

Culture Plates

Cells were cultured on plates coated with 100 ng/mL rat fibronectin in phosphate-buffered saline (PBS; 1×, without Ca and Mg). Ten-centimeter plates (for general maintenance) and 6- to 96-well plates are used as needed. Coating was done for at least one hour at 37° C., 2 hours at room temperature, or overnight at 4° C.

MAPC Media

For rat cell culture, the media contains 60% low glucose Dulbecco's Modified Eagle Media (DMEM), 40% MCDB-201, 1× insulin-transferrin-selenium, 1× linoleic acid, bovine serum albumin, $10^{-9}$ M dexamethasone, $10^{-4}$ M ascorbic acid 3-phosphate, 100 units of penicillin, 1000 units of streptomycin, 2% fetal bovine serum, 10 ng/mL human platelet-derived growth factor, 10 ng/mL mouse epidermal growth factor, and 1000 units/mL mouse leukemia inhibitory factor. Mouse cells can be cultured in similar media with the following modifications: 1× selenium-insulin-transferrin-ethanolamine is used instead of ITS, a combination of 0.2 mg/mL LA-BSA and 0.8 mg/mL powdered bovine serum albumin is added instead of using only LA-BSA, 1× chemically-defined lipid concentrate is included and dexamethasone is not included. β-mercaptoethanol is added freshly to both types of media.

Serum lots were tested for speed of growth, correct cell morphology, expression of Oct-4, and the ability for cells to differentiate into the various lineages.

Isolation

Cells are suspended in media and plated at six million cells per well on a fibronectin-coated plate. Cells will not all be attached so the medium is not removed. Instead, fresh medium should be added. In the second week, most of the cells will have attached. In the third week, cells are replated at 80% confluence or at about $2 \times 10^4$ cells/cm$^2$. Once the cells are at 100% confluence, they are replated at 80% confluence. After culturing for about a month, column depletion is done to remove CD 45$^+$ and Terr 119$^+$ cells from the culture. After depletion, the cells are kept at a density of about 1 to $2 \times 10^2$ cells/cm$^2$. When cell-cell contact is seen, usually after about 36 to 48 hours, the cells are split or replated.

Maintenance

Every 36 to 48 hours the cells are split or the media changed. Small amounts of trypsin can be effective because the cells are small and lightly attached. Therefore, they can be removed from the plate quickly. Larger cells that are more strongly attached are likely to be differentiating and therefore are not desirable.

Media pH is important in cell culture. Keeping the incubators at proper $CO_2$ and $O_2$ levels maintains the correct culture pH of 7.2. The $CO_2$ level should be at 5.5 to 6%, and the $O_2$ level is kept low, at about 5%. These levels also reduce cytogenetic abnormalities.

Freezing and Thawing.

Freezing is done frequently whenever there are extra cells and particularly in early passages after depletion. Two-step freezing process can be used. The first consists of 80% MAPC media and 20% FBS, and the second contains 60% MAPC media, 20% FBS, and 20% DMSO. Freezing is done as quickly as possible for highest viability. Thawing is optimally done quickly as well.

Example 3

This disclosure is from Subramanian et al.

Culture Medium

The following are mixed for the medium. 60% Dulbecco's Modified Eagle medium (DMEM) low (1 g/l) glucose, 40% MCDB-201 solution at pH 7.2, 1× Insulin-transferrin-selenium (ITS), 1× Linoleic acid-Bovine serum albumin (LA-BSA), 100 IU/ml Penicillin and 100 μg/ml Streptomycin, $10^{-4}$M 1-Ascorbic acid (add 256 mg of 1-Ascorbic acid to 100 ml PBS), 2% qualified FBS, 10 ng/ml human PDGF-BB, 10 ng/ml mouse EGF, 0.05 μM dexamethasone, $10^3$ units/ml mouse leukemia inhibitory factor (LIF), 55 uM fresh β2-mercaptoethanol. Plated cells are incubated with 5% oxygen and 5-6% $CO_2$.

Flow Cytometry

Antibodies: mouse anti-rat CD31-PE (TLD-3A12, BD Pharmingen), mouse anti-rat CD44-FITC (OX-49, BD Pharmingen), goat Oct3/4 (Santa Cruz). (2.) Isotype controls: Mouse IgG$_1$-PE, Mouse IgG$_{2a}$-FITC, Goat IgG, and Donkey anti-goat-Cy3 as secondary antibody for Oct4 staining. (3) Prepare formaldehyde fixation solution by diluting 400 ml of 10% Ultrapure Formaldehyde in 600 ml PBS. (4) SAP buffer—0.1% (w/v) saponin, 0.05% (w/v) sodium azide in PBS, SAP serum buffer—SAP buffer with 10% donkey serum.

Immunocytochemistry (1.) Fish skin gelatin (in water). (2.) 0.3% (v/v) hydrogen peroxide solution (30% w/w) in methanol. (3.) 0.2% Triton X-100 solution for permeabilization: (4.) Antibodies: Goat Oct3/4 and biotin-labeled donkey anti-goat secondary antibody in Dako Real Antibody diluent. (5.) Vectastain ABC kit (Vector Laboratories). (6.) Dako Liquid DAB and substrate chromogen system containing Substrate Buffer and DAB and Chromogen (Dako).

Multilineage Differentiation Capacity

Low density is used for neuroectodermal differentiation, while endodermal differentiation is performed at 100% confluency and for endothelial differentiation 80-90% confluency is used. For endothelial differentiation, the cell seeding density is 60,000 cells/cm$^2$. For neuroectoderm differentiation, cells are plated (plates precoated with 0.1% gelatin solution) at 1,500 cells/cm$^2$ in N2B27 medium for two days. On day 2, the medium is replaced with NSE medium. On about day 9 small clusters of cells detach from the plastic and start forming neurosphere-like structures.

The invention claimed is:

1. A method to produce extra-embryonic endodermal precursor cells that express extra-embryonic endodermal precursor genes, the method comprising culturing a blastocyst in a culture medium containing platelet-derived growth factor under conditions of reduced oxygen to produce the extra-embryonic endodermal precursor cells wherein the conditions for reduced oxygen include conditions less than about 20%.

2. The method of claim 1 wherein the oxygen concentration is about 10% or less.

3. The method of claim 2 wherein the oxygen concentration is about 5%.

4. The method of claim 1, wherein the extra-embryonic precursor cells express one or more transcription factors selected from the group consisting of oct4, rex-1, Ecats, Gata4, Gata6, Sox7, Sox17, Foxa2, HNF1Beta, and HNF4alpha.

5. The method of any one of claims 1-3 and 4 wherein the blastocysts are cultured without a cellular feeder layer.

6. The method of any one of claims 1-3 and 4, wherein the serum concentration is about 2% to about 5%.

7. The method of any one of claims 1-3 and 4, wherein the serum concentration is about 2%.

* * * * *